United States Patent [19]

Hollenbeck

[11] 4,237,451
[45] Dec. 2, 1980

[54] METHOD AND MEANS FOR CONTINUOUSLY SAMPLING A FLUID

[75] Inventor: Keith E. Hollenbeck, Mountain View, Calif.

[73] Assignee: Spectrex Corporation, Redwood City, Calif.

[21] Appl. No.: 10,903

[22] Filed: Feb. 9, 1979

[51] Int. Cl.³ .............................................. G08B 21/00
[52] U.S. Cl. ...................................... 340/606; 73/28; 340/573; 417/45
[58] Field of Search ............... 340/606, 607, 664, 573, 340/648; 417/45, 43; 73/28, 421.5 R

[56] References Cited

U.S. PATENT DOCUMENTS

| | | | |
|---|---|---|---|
| 3,501,899 | 3/1970 | Allen | 417/43 |
| 3,956,940 | 5/1976 | Guild | 73/28 |
| 4,063,824 | 12/1977 | Baker et al. | 417/43 |
| 4,159,635 | 7/1979 | Sehmel | 73/28 |

Primary Examiner—Glen R. Swann, III
Attorney, Agent, or Firm—A. C. Smith

[57] ABSTRACT

An improved air-sampling pump of miniature size ideally suited for carrying on a person includes monitoring circuitry which controls motive pump-energizing signal applied to an air pump to ensure that sampled air is pumped through a test chamber at a substantially constant rate over an extended period of time and also includes alarm circuitry which provides comtemporary and residual indications of interrupted flow rate during the sampling period.

7 Claims, 3 Drawing Figures

METHOD AND MEANS FOR CONTINUOUSLY SAMPLING A FLUID

BACKGROUND AND SUMMARY OF THE INVENTION

Contemporary industrial hygiene practices frequently include sampling the air that an industrial worker breathes during his work shift in order to provide information about the contaminants which the worker was exposed to during his work shift. Coal mines and asbestos factories are just a few of the many work sites which are currently under close inspection by hygienists for private and governmental agencies as part of a major effort directed toward reducing the amount of airborne hazardous substances that workers are exposed to at such work sites. Air samples periodically taken in close proximity to workers and accumulated over a given work shift provide a rough indication of the total exposure to airborne substances that such workers suffered. However, such periodic sampling may miss intermittent peak periods of high-level contaminant exposure suffered, for example, when a worker moves about from one area to another.

In accordance with the present invention, a personal-size, air-sampling unit is carried by the worker throughout his entire work shift, and operates continuously to move ambient air samples through a contained test chamber at a substantially constant flow rate. The contaminants accumulated in the test chamber over the period of the work shift can thus be analyzed to provide indication of type and degree of airborne health hazard to which the worker was exposed during his work shift. In addition, the present invention provides immediate audible alarm in response to interruption of air flow and also provides an interrogatable residual alarm to indicate that an interruption of air flow for a sufficiently long period perhaps to invalidate test results occurred some time during the period of operation. In this way, the air-sampling unit carried by a worker throughout his work shift may be turned in after work for subsequent analysis of accumulated contaminants. Requisite treatment or corrective measures may thereafter be administered as required in response to the analysis of such contaminants.

DESCRIPTION OF THE PREFERRED EMBODIMENT

Figure 1A:
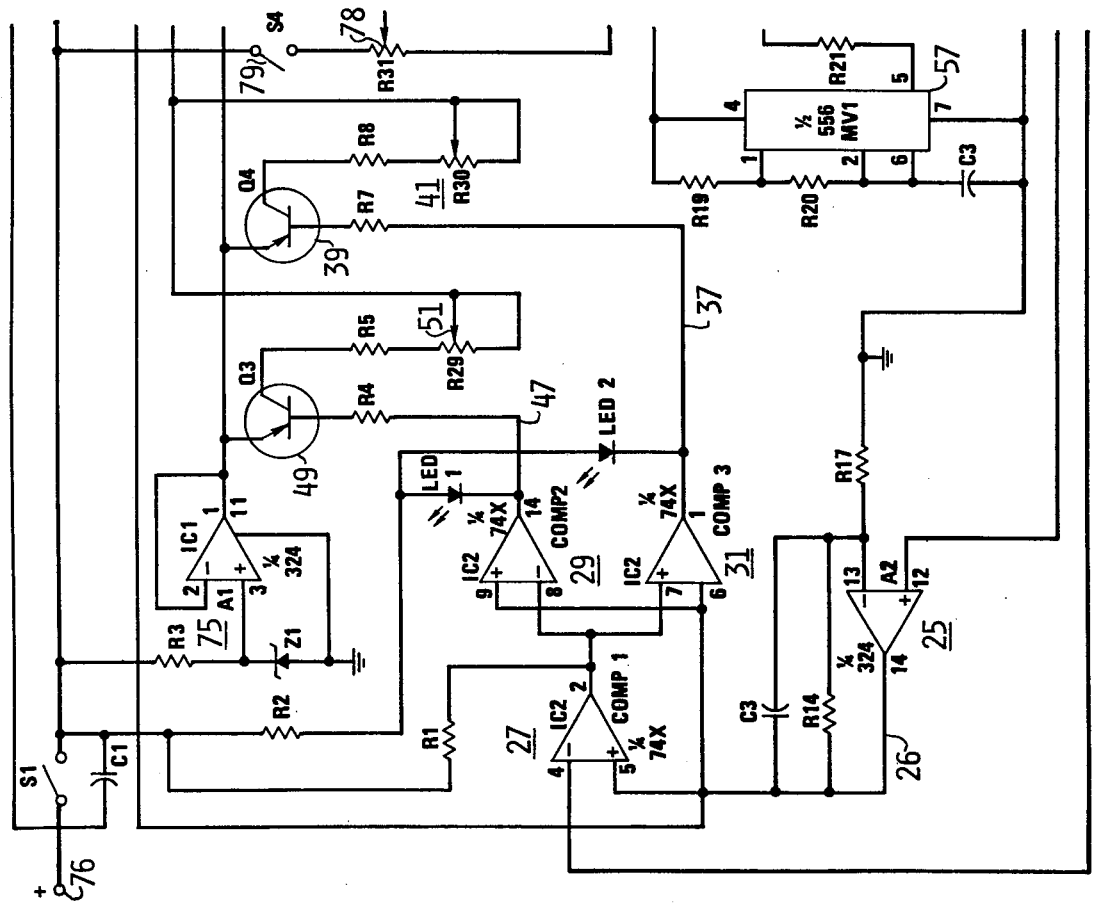
FIGS. 1A and 1B comprise a block pictorial diagram which illustrates one embodiment of the present invention.
Figure 1B:
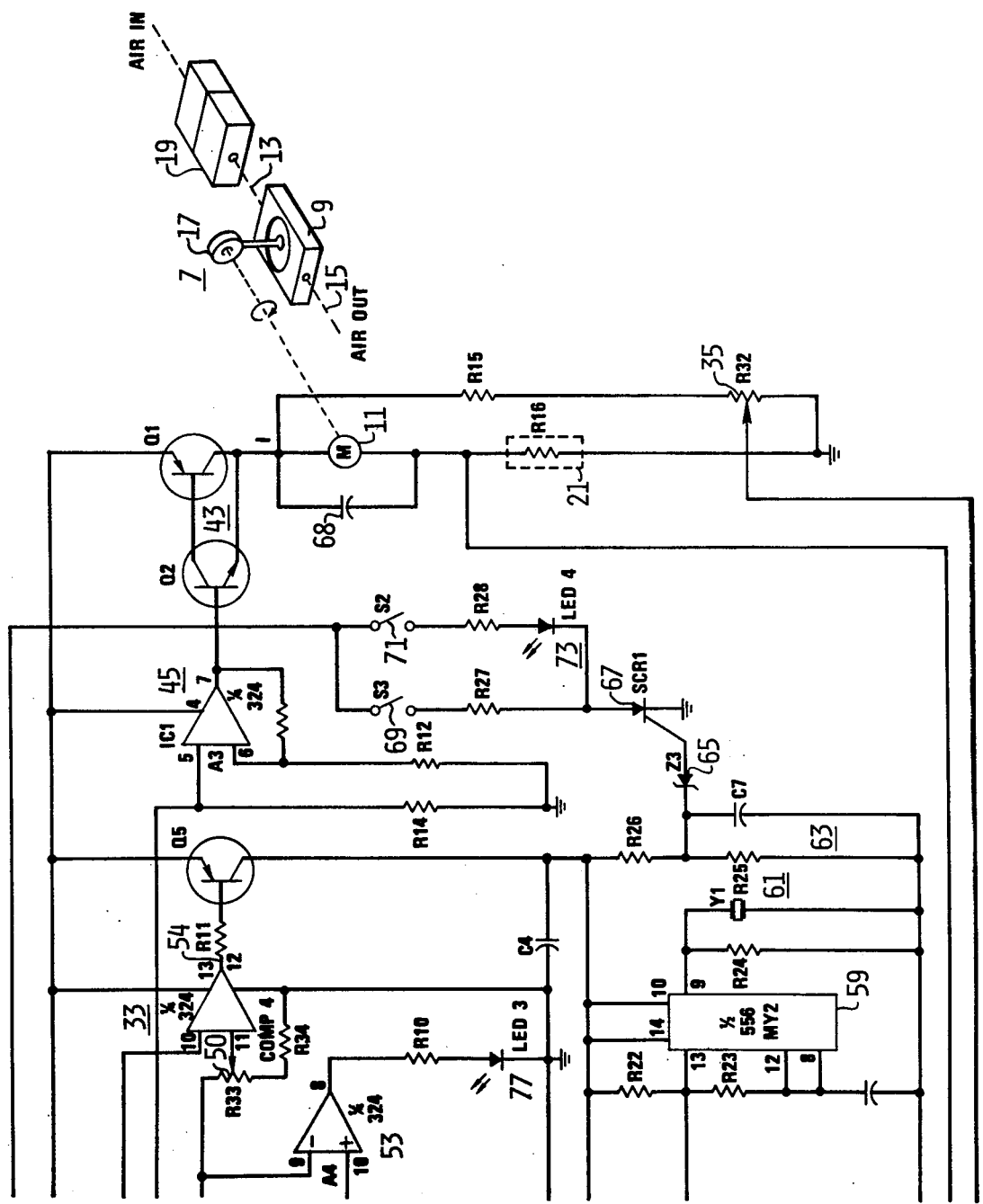

Referring now to the diagram of FIG. 1, there is shown a pump mechanism 7 which is driven by a motor 11. The pump mechanism 7 may include a bellows-type pumping chamber 9 with associated check valves at inlet 13 and outlet 15 to assure the movement of air through the chamber 9 in response to rotation of the crank or eccentric cam 17 that is coupled to the shaft of motor 11. The air that is pumped through the pumping chamber 9 is drawn through a test chamber 19 which may, for example, contain a filter for trapping particulate contaminants or may contain reactive ingredients that form no part of this invention and that alter properties in a measurable way in response to certain gaseous contaminants that are sampled.

Figure 2:
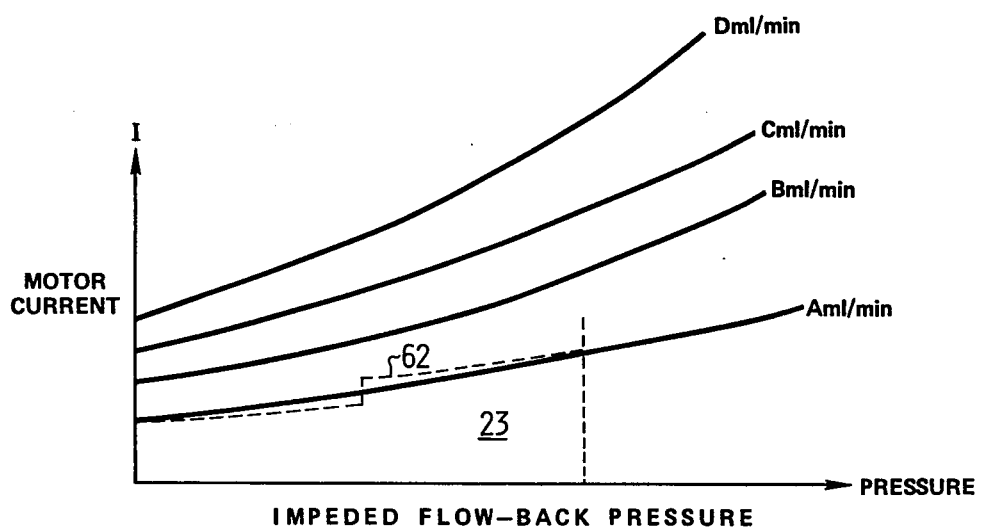
FIG. 2 is a graph showing the required motor current to maintain substantially constant air flow rate therethrough against varying air-flow obstruction.

The motor is connected in a circuit which monitors the operation of the motor and pump to assure that the flow of air remains substantially constant over an extended operating period, despite the gradual obstruction of air passage through the test chamber 19 with resulting pressure drop or differential across the chamber as the filter therein clogs up with accumulated particles. This is accomplished by monitoring the current through the motor 11 via network 21. In one embodiment of the present invention, this network 21 may be a linear resistor where the motor 11 is a permanent magnet-type D.C. motor that drives a pumping mechanism 7 to establish a substantially constant flow rate of about 2 liters of air per minute through the test chamber 19. Over a range 23 of varying back pressures of a few millimeters of mercury, as shown in the graph of FIG. 2, attributable to clogging of the filter in test chamber 19, the relationship between motor current I and the back pressure against which the pump operates is sufficiently linear to permit the use of a simple resistor in network 21. However, where the relationship between motor current and back pressure is unacceptably nonlinear, the network 21 may include additional active or passive elements to provide a nonlinear transform impedance that more accurately represents the characteristics of motor current required to maintain a substantially constant, selected rate of air flow through the test chamber 19.

The signal which appears across the network 21 in response to the motor current I therethrough is amplified by amplifier circuit 25 and is applied to one input of each of comparators 27, 29, 31 and 33. Another input of comparator 27 receives the selected portion of the voltage across the motor 11 (as set by potentiometer 35) which is normally higher than the signal applied to the one input of comparator 27 by the amplifier circuit 25. The resulting low output 37 enables transistor 39 to activate potentiometer 41 as the control for setting motor current under light load. This signal from potentiometer 41 is applied via amplifier 45 to the regulating transistors 43 which assure that the current through the motor is sufficient to maintain substantially constant flow of air through the chamber 19 as the differential pressure thereacross increases, and as battery power decreases over long periods of operation.

As motor current I increases to maintain constant air flow against increasing back pressure, the amplified signal at the one input to comparator 27 exceeds the portion of signal from potentiometer 35 provided by the setting thereof and the resulting low output 47 from comparator 29 enables transistor 49 to activate potentiometer 51 as the control for setting motor current under heavier load. This signal is then amplified by amplifier 45 and is applied to the regulating transistors 43 which assure that adequate current is supplied to the motor 11 to maintain substantially constant air flow rate through the chamber 19 under conditions of increased back pressure (i.e., heavier motor load). The resulting current profile as a function of motor load 62 is shown in FIG. 2. An integrating capacitor 68 is connected across the motor 11 to smooth the transition in drive current attributable to the switching over from one current setting 41 to the other current setting 51.

The reference signal set by potentiometer 50 and applied to the other input of comparator 33 sets the motor current limit (i.e. pump back pressure) at which an audible alarm is sounded. Thus, if the air inlet to chamber 19 becomes obstructed by clothing, foreign objects, or the like, the resulting current supplied to the motor 11 produces a high level output signal 26 from amplifier 25 which exceeds the reference signal applied to comparator 33. This produces a low output 54 which enables transistor Q5 to activate the alarm circuits connected thereto. The multivibrator including elements 57, 59, etc., thus supplies an oscillatory signal at audible frequency to the piezoelectric device 61 which produces an audible alarm signal that should alert the user to the obstruction condition at the air inlet to chamber 19. If the obstruction condtion (and high motor current) persists for a long period, the R-C timing circuit 63 provides an exponentially-increasing voltage which eventually exceeds the Zener back voltage of diode 65 and this triggers the controlled rectifier 67 into conduction. With switch 69 normally closed during pump operation, a conduction-sustaining current flows through the controlled rectifier 67 to preserve in this one-bit memory an indication of the occurrence of a low-flow (or no-flow) condition for a period sufficiently long (as determined by the R-C time constant) to adversely affect the air-sampling test results. This memory bit may be interrogated when the unit is turned in for analysis simply by closing normally-open switch 71 to see if the LED light source 73 is activated. Light from source 73 thus indicates that an obstruction at the air inlet to chamber 19 persisted sufficiently long at some time during the operating period perhaps to adversely affect air-sampling test results.

Comparator 53 is connected to the regulated output of the power source regulator 75 and to the power input terminal 76 via potentiometer 78 to provide an output that is coupled to light source 77. Potentiometer 78 may be factory set to provide a light output that indicates whether the batteries (which are connected to terminal 76) are still "good" when tested by closing switch 79.

Therefore, the air-sampling method and means of the present invention responds to the transfer function that relates motor current and air flow rate in order to provide substantially constant rate of air flow through a test chamber over an extended operating period, substantially independently of increasing opposition to air flow attributable, for example, to accumulated contaminants in the test chamber. Also, the present invention signals an inoperative air-sampling condition and preserves an indication that such a condition persisted for an unacceptably long period of time.

I claim:

1. Fluid-sampling apparatus including fluid-pumping means arranged to pump fluid through a test chamber, the apparatus comprising:
    motor means coupled to the fluid-pumping means for pumping fluid through the test chamber at a flow rate which is determined by the characteristics of applied motor current and fluid pressure differential across the test chamber;
    monitoring means coupled to the motor means for producing a signal proportional to the motor current therethrough; and
    circuit means responsive to the signal from said monitoring means for supplying current to said motor means through the monitoring means to maintain the flow rate of fluid through the test chamber substantially constant.

2. Fluid-sampling aparatus as in claim 1 comprising:
    comparator means coupled to the monitoring means for producing an output in response to the signal therefrom attaining a selected value; and
    means responsive to said output for producing an alarm indication which is indicative of an insufficient flow rate of fluid through the test chamber.

3. Fluid-sampling apparatus as in claim 2 comprising:
    storage means coupled to receive said output for storing a logic state indicative of the occurrence of an alarm indication; and
    accessing means coupled to the storage means for selectively interrogating the storage means to determine the occurrence of an alarm indication.

4. Fluid-sampling apparatus as in claim 3 comprising timing means connected to apply said output to the storage means for storing said logic state therein after a time interval of alarm indication determined by the timing means.

5. The method of sampling a fluid by pumping fluid samples through a test chamber, the method comprising the steps of:
    identifying the characteristic relationship between the flow rate of fluid through the test chamber at selected differential pressures thereacross and a motive pump-energizing signal required to establish such flow rate of fluid;
    transforming the motive pump-energizing signal to a monitor signal according to a relationship therebetween which is representative of said characteristic relationship; and
    regulating the motive pump-energizing signal in response to the monitor signal to maintain the flow rate of fluid through the test chamber substantially constant over a selected range of differential pressures thereacross.

6. The method according to claim 5 comprising the steps of:
    detecting the condition of monitor signal attaining a value in excess of a selected limit value in response to obstruction of fluid flow through the test chamber; and
    providing an output indication of the detected condition.

7. The method according to claim 6 comprising the step of storing an interrogatable logic condition indicative of persistence of the detected condition for longer than a selected period of time.

* * * * *